United States Patent
White et al.

(10) Patent No.: US 10,737,992 B2
(45) Date of Patent: Aug. 11, 2020

(54) METHODS OF FORMING PROPYLENE AND ALKYLATE

(71) Applicant: Lyondell Chemical Technology, L.P., Houston, TX (US)

(72) Inventors: Daniel F. White, Houston, TX (US); Lei Zhang, League City, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 16/293,906

(22) Filed: Mar. 6, 2019

(65) Prior Publication Data

US 2019/0276378 A1 Sep. 12, 2019

Related U.S. Application Data

(60) Provisional application No. 62/639,226, filed on Mar. 6, 2018.

(51) Int. Cl.

| | | |
|---|---|---|
| *C07C 2/36* | (2006.01) | |
| *C07C 6/04* | (2006.01) | |
| *B01J 31/02* | (2006.01) | |
| *B01J 31/14* | (2006.01) | |
| *C07C 2/24* | (2006.01) | |
| *C07C 2/30* | (2006.01) | |
| *C07C 2/58* | (2006.01) | |

(52) U.S. Cl.
CPC ............ *C07C 6/04* (2013.01); *B01J 31/0271* (2013.01); *B01J 31/143* (2013.01); *C07C 2/24* (2013.01); *C07C 2/30* (2013.01); *C07C 2/36* (2013.01); *C07C 2/58* (2013.01); *C07C 2523/755* (2013.01); *C07C 2531/14* (2013.01); *C07C 2531/24* (2013.01)

(58) Field of Classification Search
CPC . B01J 31/0271; B01J 31/143; C07C 2531/14; C07C 2531/24; C07C 2/24; C07C 2/30; C07C 6/04
See application file for complete search history.

(56) References Cited

U.S. PATENT DOCUMENTS

| | | | |
|---|---|---|---|
| 3,321,549 A | 5/1967 | Roest et al. | |
| 4,242,531 A | 12/1980 | Carter | |
| 4,476,341 A | 10/1984 | Mathys | |
| 4,868,342 A | 9/1989 | Verson | |
| 5,260,499 A | 11/1993 | Wu | |
| 5,414,178 A | 5/1995 | Wu | |

(Continued)

FOREIGN PATENT DOCUMENTS

| | | |
|---|---|---|
| WO | 2009015118 A2 | 1/2009 |
| WO | 2012051427 A1 | 4/2012 |
| WO | 2014123972 A1 | 8/2014 |

OTHER PUBLICATIONS

The Extended European Search Report for EP19159253.4 dated Jul. 22, 2019.

*Primary Examiner* — Sharon Pregler

(57) ABSTRACT

Methods of forming propylene and alkylate are provided. The methods may include providing a stream that includes n-butenes, and contacting the stream with ethylene in the presence of a disproportionation catalyst to form a stream that includes propylene. Propylene then may be removed from the stream, and the stream may be disposed in an alkylation unit to form alkylate.

20 Claims, 2 Drawing Sheets

(56) References Cited

U.S. PATENT DOCUMENTS

| | | | |
|---|---|---|---|
| 7,728,185 B2 * | 6/2010 | Senetar | C07C 4/06 585/259 |
| 8,395,005 B2 | 3/2013 | Coleman et al. | |
| 2009/0030252 A1 | 1/2009 | Senetar et al. | |
| 2013/0172647 A1 * | 7/2013 | Coleman | C07C 2/36 585/329 |

* cited by examiner

METHODS OF FORMING PROPYLENE AND ALKYLATE

CROSS-REFERENCE TO RELATED APPLICATIONS

This application claims the benefit of priority to U.S. Provisional Patent Application No. 62/639,226 filed on Mar. 6, 2018, which is incorporated herein by reference in its entirety.

BACKGROUND

Ethylene dimerization typically offers higher quality butene feeds for both propylene production via ethylene/butene disproportionation (metathesis), and alkylate production with isoparaffins, usually due to increased throughputs from the substantially butane-free feed.

A butenes product from ethylene dimerization can be fed to a propylene unit and an alkylation unit operated in parallel, but such systems typically suffer from one or more disadvantages. When a disproportionation unit is operated separately, the concentration of 2-butene in the recycled butenes usually is lower than the concentration of 2-butene in the butenes obtained from ethylene dimerization. The recycled butenes are believed to have an increased 1-butene concentration due at least in part to thermodynamic equilibrium. As a result, the propylene selectivity and/or the subsequent yield usually are lower than the propylene selectivity and/or the subsequent yield achieved with a fresh butenes feed from ethylene dimerization.

Moreover, when an alkylation unit uses butenes for an ethylene dimerization process, a de-ethanizer typically is required to remove unconsumed ethylene in order to reduce or avoid excessive sulfuric acid catalyst consumption during alkylation.

There remains a need for methods that overcome one or more of the foregoing disadvantages.

BRIEF SUMMARY

Provided herein are methods of forming propylene and alkylate that may increase propylene selectivity and/or yield, increase alkylate yield, reduce acid catalyst loss in alkylation processes, or a combination thereof. The methods provided herein also may permit $C_5$ olefins to be included in an alkylation feed, thereby possibly reducing the overall $C_4$ splitter bottom low-value byproduct.

In some embodiments, the methods provided herein include providing a stream including n-butenes; contacting the stream including n-butenes with a second stream including ethylene in the presence of a disproportionation catalyst to form a stream including propylene and $C_{4+}$ olefins; removing propylene from the stream including propylene and $C_{4+}$ olefins to form a stream including $C_{4+}$ olefins; and contacting the stream including $C_{4+}$ olefins with a stream including isobutane in the presence of an alkylation catalyst to form alkylate. In some embodiments, the stream including n-butenes includes 2-butenes. The 2-butenes may include cis-2-butenes and trans-2-butenes. In some embodiments, the providing of the stream including n-butenes includes contacting a first stream including ethylene with a dimerization catalyst to form the stream including n-butenes, and the stream including n-butenes may also include unconsumed ethylene.

In some embodiments, the methods provided herein include contacting a first stream including ethylene with a dimerization catalyst to form a stream including n-butenes and $C_{6+}$ olefins; removing the $C_{6+}$ olefins from the stream including n-butenes and $C_{6+}$ olefins to form a stream including n-butenes; contacting the stream including n-butenes with a second stream including ethylene in the presence of a disproportionation catalyst to form a stream including ethylene, propylene, and $C_{4+}$ olefins; removing ethylene from the stream including ethylene, propylene, and $C_{4+}$ olefins to form a stream including propylene and $C_{4+}$ olefins and a third stream including ethylene, wherein the third stream including ethylene is (i) combined with the second stream including ethylene, (ii) combined with the stream including n-butenes, or (iii) disposed in a disproportionation unit that contains the disproportionation catalyst; removing propylene from the stream including propylene and $C_{4+}$ olefins to form a stream including $C_{4+}$ olefins; and contacting the stream including $C_{4+}$ olefins with a stream including isobutane in the presence of an alkylation catalyst to form alkylate.

DETAILED DESCRIPTION

Figure 1:
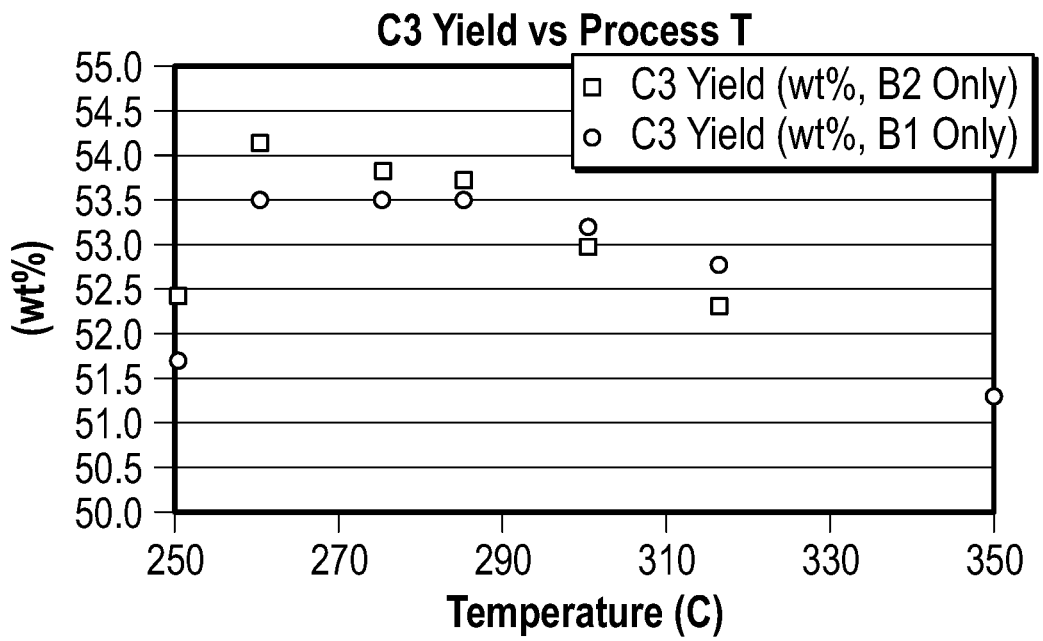
FIG. 1 depicts the propylene yields at different process temperatures for embodiments of disproportionation reactions performed on feeds including 2-butenes or 1-butenes.

Provided herein are methods that may include operating propylene and alkylation processes in tandem. In some embodiments, a fresh butenes feed obtained from ethylene dimerization is fed to a disproportionation unit to increase, and possibly maximize, propylene selectivity, propylene yield, or a combination thereof. Unconverted ethylene and product propylene may then be removed from the resulting stream to produce a stream including the remaining butenes and a $C_5$ olefin byproduct from the disproportionation unit, which may be forwarded to an alkylation unit. The stream forwarded to the alkylation unit may increase, or possibly maximize, alkylate yield, and reduce, or possibly minimize, acid catalyst loss.

Not wishing to be bound by any particular theory, it is believed that embodiments of the processes provided herein can increase, or possibly maximize, propylene yield because the processes maintain a relatively high ratio of 2-butene:1-butene in the feed stream forwarded to a disproportionation unit. The product of ethylene dimerization typically includes 1-butene and 2-butene, and, in some embodiments, a selective catalyst is used to increase the ratio of 2-butene:1-butene, which can be advantageous because 2-butene is favored for propylene production. Therefore, a higher ratio of 2-butene:1-butene can result in a higher yield of propylene. Due to the fact that 2-butene is favored for propylene production, the product effluent from a disproportionation unit generally has a greater content of 1-butene than the feed provided to the disproportionation unit. Since the product effluent from a disproportionation unit is not recycled and fed back to the disproportionation unit in embodiments of the methods provided herein, a higher ratio of 2:butene: 1-butene in the feed sent to the disproportionation unit may be maintained; therefore, an improved propylene selectivity and/or yield may be achieved. Instead of recycling the product effluent of a disproportionation unit, the unconverted butenes of the product effluent, in some embodiments, are processed in an alkylation unit, which generally has no preference, or at least a reduced preference, for one of 1-butene and 2-butene.

In some embodiments, the methods provided herein include providing a stream including n-butenes; contacting the stream including n-butenes with a second stream including ethylene in the presence of a disproportionation catalyst to form a stream including propylene and $C_{4+}$ olefins; removing propylene from the stream including propylene and $C_{4+}$ olefins to form a stream including $C_{4+}$ olefins; and contacting the stream including $C_{4+}$ olefins with a stream including isobutane in the presence of an alkylation catalyst to form alkylate.

As used herein, the phrases "$C_{4+}$ olefins", "$C_{6+}$ olefins", and the like, refer to olefin samples containing olefins having 4 or more carbon atoms, or 6 or more carbon atoms, respectively. For example, "$C_{4+}$ olefins" may include butenes, pentenes, hexenes, heptenes, octenes, etc., or a combination thereof. As a further example, "$C_{6+}$ olefins" may include hexenes, heptenes, octenes, etc., or a combination thereof.

As used herein, the phrase "alkylate" generally refers to an alkylation reaction product. For example, "alkylate" may include a substance produced by adding one or more alkyl groups to a compound.

In some embodiments, the methods provided herein include contacting a first stream including ethylene with a dimerization catalyst to form a stream comprising n-butenes; contacting the stream including n-butenes with a second stream including ethylene in the presence of a disproportionation catalyst to form a stream including propylene and $C_{4+}$ olefins; removing propylene from the stream including propylene and $C_{4+}$ olefins to form a stream including $C_{4+}$ olefins; and contacting the stream including $C_{4+}$ olefins with a stream including isobutane in the presence of an alkylation catalyst to form alkylate.

In some embodiments, the stream including n-butenes includes 2-butenes. As used herein, the term "n-butenes" generally refers to linear alkenes having four carbon atoms and at least one double bond. In some embodiments, the stream including n-butenes includes 1-butenes and 2-butenes. The 2-butenes of the stream including n-butenes may include cis-2-butenes, trans-2-butenes, or a combination thereof.

In some embodiments, the stream including n-butenes includes 2-butenes at a weight percentage of about 50% to about 100%, based on the weight of the stream including n-butenes. In some embodiments, the stream including n-butenes includes 2-butenes at a weight percentage of about 60% to about 100%, based on the weight of the stream including n-butenes. In some embodiments, the stream including n-butenes includes 2-butenes at a weight percentage of about 70% to about 100%, based on the weight of the stream including n-butenes. In some embodiments, the stream including n-butenes includes 2-butenes at a weight percentage of about 80% to about 100%, based on the weight of the stream including n-butenes. In some embodiments, the stream including n-butenes includes 2-butenes at a weight percentage of about 90% to about 100%, based on the weight of the stream including n-butenes.

In some embodiments, the methods provided herein include contacting a first stream including ethylene with a dimerization catalyst to form a stream including n-butenes, or a stream including n-butenes and unconverted ethylene. Generally, any catalyst capable of dimerizing ethylene to form n-butene may be used as the dimerization catalyst in the methods provided herein. In some embodiments, a dimerization catalyst includes a transition metal catalyst. The transition metal catalyst may include Ti, Cr, Ni, Fe, Zr, V, or a combination thereof.

In some embodiments, a dimerization catalyst also includes a cocatalyst. Non-limiting examples of cocatalysts that may be used in the methods provided herein include an aluminum alkyl, an organoborane, or a combination thereof. Non-limiting examples of aluminum alkyl cocatalysts include triethylaluminum (TEA), ethylaluminum dichloride (EADC), or a combination thereof. In some embodiments, the organoborane cocatalyst includes tris(pentafluorophenyl)borane.

The dimerization catalyst can be a homogeneous catalyst or a heterogeneous catalyst. Examples of suitable homogeneous catalysts are disclosed in U.S. Pat. Nos. 3,321,546, 4,242,531, 4,476,341, 5,260,499 and 5,414,178, which are incorporated herein by reference. One such catalyst includes a nickel compound and an organo aluminum compound. Suitable nickel compounds include nickel salts of a mono- or dicarboxylic acid, such as an acid having 5 to 20 carbon atoms, such as nickel oleate, nickel dodecanoate, or nickel octanoate. Other nickel compounds include coordination complexes of organic phosphines with nickel salts. Examples of such complexes are nickel bis(triethylphosphine) chloride [Ni(Et$_3$P)$_2$Cl$_2$], nickel bis(triphenylphosphine) octanoate, nickel bis(triphenylphosphine) chloride, nickel bis(tributylphosphine) chloride, and nickel bis(tricyclohexylphosphine) chloride. Suitable organo aluminum compounds include those having 1 to 2 alkyl groups and 1 to 2 halogen atoms per aluminum atom. The alkyl groups, in some embodiments, have 1 to 5 carbon atoms. The halogen, in some embodiments, is chlorine. In some embodiments, the dimerization catalyst includes nickel bis(tributylphosphine) chloride and ethyl aluminum dichloride. The molar ratio Ni:Al may be 1:2 to 1:6.

In some embodiments, the dimerization catalyst includes a cocatalyst, and dimerizes ethylene to create one or more of the following products:

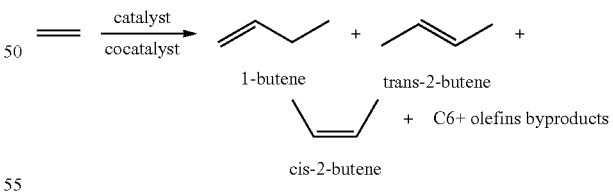

In some embodiments, the disproportionation reactions described herein favor 2-butenes (both cis- and trans-isomers). Therefore, a dimerization catalyst that increases or maximizes the creation of 2-butenes from the ethylene dimerization may be selected, thereby possibly allowing a higher propylene yield to be achieved. As depicted at FIG. 1, propylene yields are generally higher, especially at lower process temperatures, when a feed includes 2-butenes instead of 1-butenes. FIG. 1 presents the results of an experiment conducted using a combination of isomerization catalyst magnesium oxide (MgO) and metathesis catalyst tungsten oxide ($WO_3$) supported on silicon oxide ($SiO_2$). Specifically, the catalyst loading was 1 part by weight of MgO layer on top of a physical mixture of 3 parts by weight MgO and 1 part by weight $WO_3/SiO_2$. The feed was either ethylene with butene-2 (a mixture of cis and trans isomers) or with butene-1. The process pressure was 3103 kPa and the reaction space velocity was 6.4.

Generally, a stream including ethylene and a dimerization catalyst may be contacted in any suitable reactor and under any suitable conditions to generate a stream including n-butenes. In some embodiments, a stream including ethylene and a dimerization catalyst are contacted at a temperature of at least about 35° C. For example, a stream including ethylene and a dimerization catalyst may be contacted at a temperature of about 35° C. to about 100° C., about 35° C. to about 90° C., about 35° C. to about 80° C., about 35° C. to about 70° C., about 35° C. to about 60° C., about 40° C. to about 60° C., or about 50° C. In some embodiments, a stream including ethylene and a dimerization catalyst are contacted at a pressure of at least about 344 kPa, or at least about 1034 kPa. For example, a stream including ethylene and a dimerization catalyst may be contacted at a pressure of about 344 kPa to about 10342 kPa, about 344 kPa to about 6895 kPa, about 344 kPa to about 4137 kPa, about 689 kPa to about 6895 kPa, about 1034 kPa to about 1724 kPa, about 1241 kPa to about 1379 kPa, or about 1310 kPa. In some embodiments, a stream including ethylene and a dimerization catalyst are contacted in the presence of a solvent. The solvent may include a hydrocarbon solvent, including, but not limited to, toluene, heptane, hexane, a halogenated hydrocarbon, such as chlorobenzene or chloroform, or a combination thereof. In some embodiments, a stream including ethylene and a dimerization catalyst are contacted at a temperature of about 35° C. to about 100° C., about 35° C. to about 90° C., about 35° C. to about 80° C., about 35° C. to about 70° C., about 35° C. to about 60° C., about 40° C. to about 60° C., or about 50° C., a pressure of about 344 kPa to about 10342 kPa, about 344 to about 4137 kPa, about 689 kPa to about 6895 kPa, about 1034 to about 1724 kPa, about 1241 kPa to about 1379 kPa, or about 1310 kPa, and in the presence of a solvent. The solvent may include a hydrocarbon solvent, including, but not limited to, toluene, heptane, hexane, or a halogenated hydrocarbon, such as chlorobenzene or chloroform, or a combination thereof.

In some embodiments, streams including n-butenes also may include $C_{6+}$ olefins. The $C_{6+}$ olefins may be removed from the streams including n-butenes prior to performing a disproportionation reaction. For example, the methods provided herein may include removing the $C_{6+}$ olefins from the stream including n-butenes prior to the contacting of the stream including n-butenes with the second stream including ethylene. The $C_{6+}$ olefins may be removed using any known techniques, including distillation.

In some embodiments, the methods provided herein include contacting a stream including n-butenes with a second stream including ethylene in the presence of a disproportionation catalyst to form a stream including propylene and $C_{4+}$ olefins. The stream including n-butenes and the second stream including ethylene may be combined prior to entering a disproportionation unit. Additionally or alternatively, the stream including n-butenes and the second stream including ethylene may be provided separately to a disproportionation unit, and contact each other in the disproportionation unit.

In some embodiments, a stream including propylene and $C_{4+}$ olefins also includes ethylene. When ethylene is present in a stream including propylene and $C_{4+}$ olefins, the methods provided herein may include removing the ethylene from the stream including propylene and $C_{4+}$ olefins to form a third stream including ethylene. The ethylene may be removed prior to removing propylene from the stream including propylene and $C_{4+}$ olefins, or the ethylene may be removed prior to contacting the stream including $C_{4+}$ olefins with isobutane.

Not wishing to be bound by any particular theory, it is believed that a stream obtained from a dimerization reaction and/or a disproportionation reaction may include some unconverted ethylene, which may be detrimental if an acid catalyst is used in a downstream alkylation reaction, because the unconverted ethylene may consume the acid catalyst, especially sulfur acid catalysts. Any known technique or de-ethanizer may be used to remove ethylene from a stream, including distillation.

When the methods provided herein include removing ethylene from the stream including propylene and $C_{4+}$ olefins to form a third stream including ethylene, the third stream including ethylene may be reacted with a stream including n-butenes in a disproportionation unit. The third stream including ethylene may be disposed in a disproportionation unit, combined with a stream including n-butenes (which may be combined with a second stream including ethylene) before the stream including n-butenes is disposed in a disproportionation unit, or combined with a second stream including ethylene before the second stream including ethylene is disposed in a disproportionation unit. In some embodiments, the methods herein include combining the second stream including ethylene and the third stream including ethylene. In some embodiments, the methods herein include combining a stream including n-butenes and the third stream including ethylene. In some embodiments, the methods herein including disposing the third stream including ethylene in a disproportionation unit that contains the disproportionation catalyst.

Generally, the disproportionation catalyst may include any catalyst capable of producing propylene when contacted with n-butenes and ethylene. For example, U.S. Pat. No. 8,395,005, which is incorporated herein by reference, discloses examples of disproportionation catalysts and processes for converting n-butenes and ethylene to propylene. In some embodiments, a disproportionation catalyst includes a transition metal oxide. The transition metal oxide may include a transition metal selected from Group VIB to Group VIIIB of the periodic table. In some embodiments, the transition metal oxide includes W, Mo, Re, Ru, or a combination thereof. The disproportionation catalyst may be a homogeneous organometallic catalyst. The disproportionation catalyst may be a solid supported catalyst. The disproportionation catalyst may be in the form of a powder or particulates. Suitable catalyst forms may include includes beads, granules, pellets, extrudates, tablets, agglomerates, honeycomb monolith, and the like, generally having a particle size of greater than 1 mm. A disproportionation catalyst also may be used in combination with an isomerization catalyst, a disproportionation catalyst promoter, or a combination thereof.

In some embodiments, the disproportionation catalyst includes tungsten oxide supported on a silica carrier. Examples of silica carriers include high purity silicas, i.e., those having a very low level of sodium (e.g., less than 2000 ppm $Na_2O$) and aluminum (e.g., less than 2000 ppm $Al_2O_3$). Generally, the silica carrier may have a surface area of at least 10 square meters per gram. In some embodiments, the surface area is at least 50 square meters per gram. To prepare a tungsten oxide-on-silica catalyst, an aqueous solution or suspension of tungsten oxide or a tungsten oxide precursor may be used to contact a silica carrier. Suitable tungsten oxide precursors are compounds that are convertible to the oxide form under calcination conditions, such as, for example, halides, sulfides, sulfates, nitrates, carboxylates, and the like, and mixtures thereof. Exemplary tungsten compounds include tungsten pentabromide, tungsten dichloride, tungsten tetrachloride, tungsten hexafluoride, tungsten trioxide, tungsten dioxydichloride, tungsten trisulfide, metatungstic acid, orthotungstic acid, ammonium phosphotungstate, ammonium metatungstate, and mixtures thereof. The tungsten oxide-on-silica catalyst, in some embodiments, is used in a fixed-bed reactor.

The disproportionation reaction generally may be performed under any conditions capable of producing propylene. In some embodiments, the disproportionation reaction is performed at a temperature of about 200° C. to about 500° C., or about 250° C. to about 400° C. In some embodiments, the disproportionation reaction is performed at a pressure of about 344 kPa to about 3448 kPa. In some embodiments, the weight hourly space velocities are about 0.2 to about 10 kg feed per kg catalyst per hour. In some embodiments, the disproportionation reaction is performed at a temperature of about 200° C. to about 500° C., or about 250° C. to about 400° C., a pressure of about 344 kPa to about 3448 kPa, and the weight hourly space velocity is about 0.2 to about 10 kg feed per kg catalyst per hour.

After a disproportionation reaction, in some embodiments, the stream including propylene and $C_{4+}$ olefins also includes 1-butene and 2-butene, and the amount of 1-butene in the stream including propylene and $C_{4+}$ olefins is greater than the amount of 1-butene in the stream comprising n-butenes. After a disproportionation reaction, in some embodiments, the stream including propylene and $C_{4+}$ olefins also includes 1-butene and 2-butene, and the amount of 1-butene in the stream including propylene and $C_{4+}$ olefins is greater than the amount of 2-butene in the stream including propylene and $C_{4+}$ olefins.

Not wishing to be bound by any particular theory, it is believed that the amount of 1-butene in a stream including propylene and $C_{4+}$ olefins obtained from a disproportionation reaction may be lower, in some embodiments, than [1] the amount of 1-butene in the stream comprising n-butenes, and/or [2] the amount of 2-butene in the stream including propylene and $C_{4+}$ olefins because, as depicted by the following reaction schemes, both the cis- and trans-isomers of 2-butene are preferred over 1-butene for propylene production:

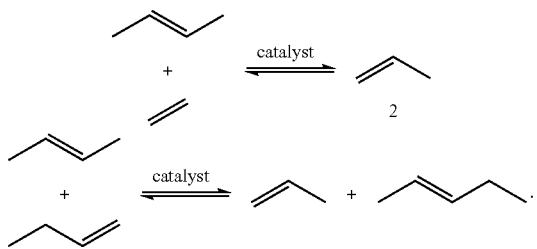

Due at least in part to the foregoing selectivity depicted in the forgoing reaction scheme, some embodiments of the processes provided herein can increase, or possibly maximize, propylene yield because the processes provided herein maintain a relatively high ratio of 2-butene:1-butene in the feed stream forwarded to a disproportionation unit, because the n-butenes obtained from a disproportionation reaction are not recycled through a disproportionation unit.

Figure 2:
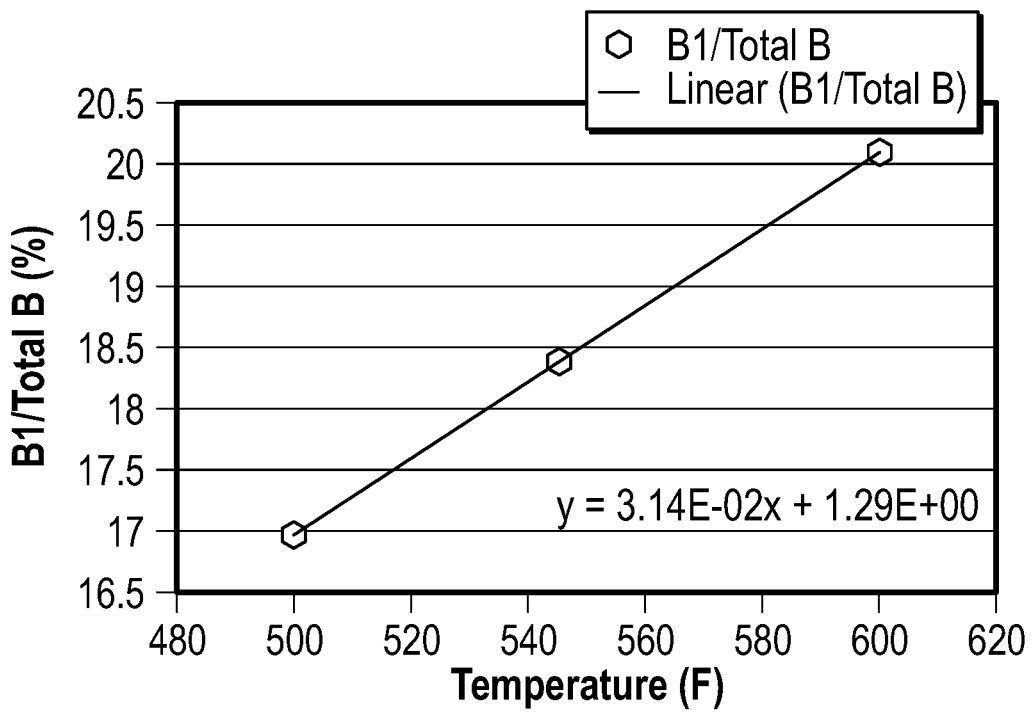
FIG. 2 depicts 1-butene/2-butene isomerization equilibrium as a function of temperature.
Figure 3:
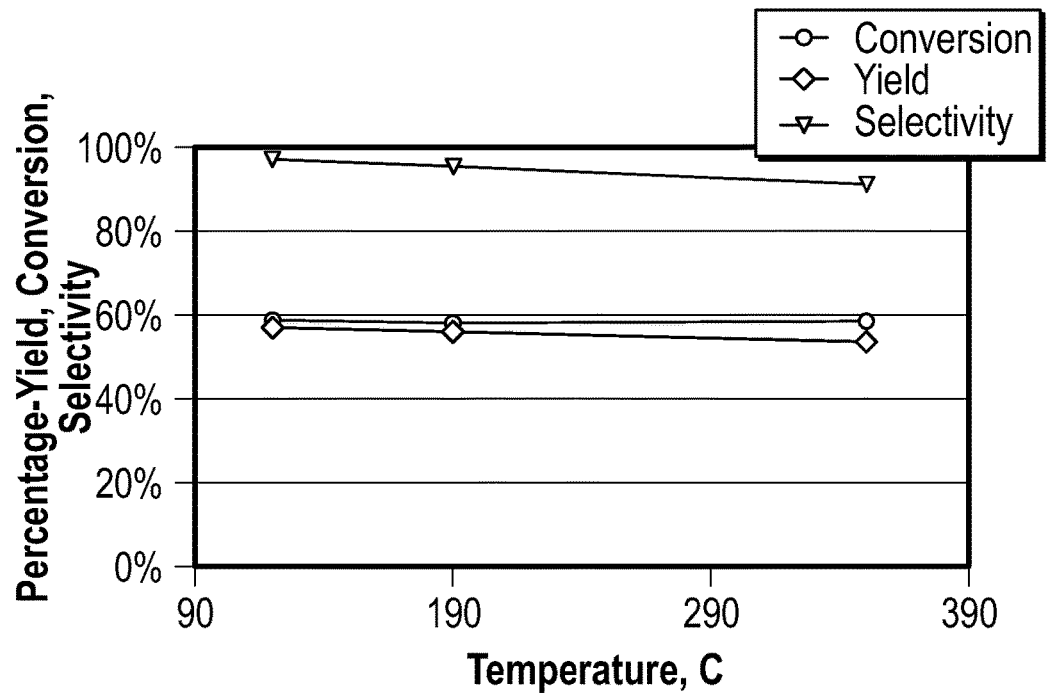
FIG. 3 depicts the conversion of n-butenes, and the yield and selectivity of propylene as a function of temperature for an embodiment of the olefin metathesis of ethylene and n-butenes (1:1 molar ratio).

Not wishing to be bound by any particular theory, it is believed that utilizing lower process temperatures, at least in certain embodiments, may increase the amount of 2-butene in a stream (thereby possibly resulting in improved or maximized propylene yield). As depicted at FIG. 2, lower process temperatures generally favor 2-butene and, as a result, improved propylene selectivity. FIG. 2 presents a measured thermodynamic equilibrium of B1/B2 isomerization. At equilibrium, the composition of B1 in total butene is not expected to be influenced by the catalyst and process conditions. Nevertheless, the equilibrium was compiled with both MgO catalyst and $K_2O$ catalyst separately under 34.5 kPa with butene-1 at WHSV of 0.016. FIG. 3 depicts modeling results for the conversion of n-butenes, and the yield and selectivity of propylene as a function of temperature for an embodiment of the olefin metathesis of ethylene and n-butenes (1:1 molar ratio) incorporating equilibria of primary and secondary metathesis reactions.

In some embodiments, the methods provided herein include removing propylene from the stream including propylene and $C_{4+}$ olefins to form a stream including $C_{4+}$ olefins. The propylene may be removed using any known technique. For example, the propylene may be removed by distillation. In some embodiments, the propylene is removed from the stream including $C_{4+}$ olefins after ethylene has been removed from the stream.

In some embodiments, the methods provided herein include contacting the stream including $C_{4+}$ olefins with a stream comprising isobutane in the presence of an alkylation catalyst to form alkylate. Generally, any alkylation catalyst capable of forming alkylate upon contacting olefins and isoparaffins may be used in the methods provided herein. In some embodiments, the alkylation catalyst may include HF, $H_2SO_4$, an ionic liquid, a zeolite, or a combination thereof.

Not wishing to be bound by any particular theory, it is believed that, unlike embodiments of the disproportionation reactions provided herein, the alkylation reactions provided herein, at least in some embodiments, demonstrate less selectivity, or no selectivity, for 2-butenes versus 1-butenes. Therefore, an increased relative amount of 1-butene in a stream provided to an alkylation unit will have less, or no, negative impact on the process. In some embodiments, isomerization of 1-butene and 2-butene may occur readily in-situ to provide similar alkylate quality. The following scheme depicts an example of butene alkylation by isobutane to octanes:

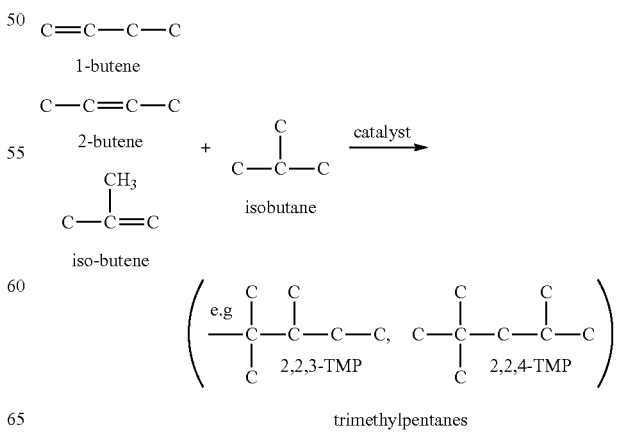

Examples of alkylation reactions and parameters may be found at U.S. Pat. No. 5,649,281, which is incorporated by reference.

Figure 4:
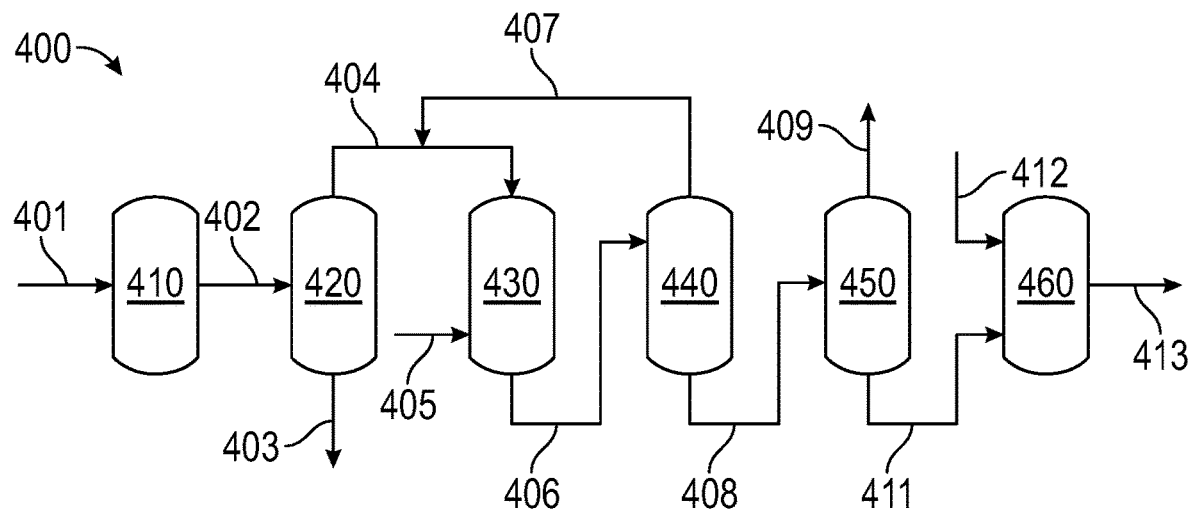
FIG. 4 depicts an embodiment of a system in which embodiments of the methods provided herein may be performed.

In some embodiments, the methods provided herein are performed in the system depicted at FIG. 4. The system 400 of FIG. 4 includes a dimerization unit 410 to which a stream 401 including ethylene is provided and contacted therein with a dimerization catalyst to form a stream 402 including n-butenes and, possibly, unconsumed ethylene. The stream 402 including n-butenes is fed to a $C_4$ splitter 420, which removes at least a portion of $C_{6+}$ olefins 403 from the stream 402 including n-butenes to form a purified stream 404 including n-butenes. The purified stream 404 including n-butenes and an ethylene stream 405 are provided to a disproportionation unit 430 in which the streams (404, 405) are contacted with a disproportionation catalyst to form a stream 406 including propylene and $C_{4+}$ olefins. The stream 406 including propylene and $C_{4+}$ olefins is then provided to a de-ethanizer unit 440 to remove at least a portion of ethylene 407 from the stream 406 including propylene and $C_{4+}$ olefins to form a purified stream 408 including propylene and $C_{4+}$ olefins. The separated ethylene stream 407 is combined with the stream 404 including n-butenes, or, in other embodiments, the separated ethylene stream 407 is fed directly to the disproportionation unit 430, combined with the ethylene stream 405, or a combination thereof. The purified stream 408 including propylene and $C_{4+}$ olefins is provided to a de-propanizer unit 450 to remove propylene from the purified stream 408 including propylene and $C_{4+}$ olefins to form a stream 410 including $C_{4+}$ olefins. The stream 411 including $C_{4+}$ olefins is provided to an alkylation unit 460, and contacted with an alkylation catalyst and a stream 412 including isobutane to produce alkylate 413.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

In the descriptions provided herein, the terms "includes," "is," "containing," "having," and "comprises" are used in an open-ended fashion, and thus should be interpreted to mean "including, but not limited to." When methods are claimed or described in terms of "comprising" various components or steps, the methods can also "consist essentially of" or "consist of" the various components or steps, unless stated otherwise.

The terms "a," "an," and "the" are intended to include plural alternatives, e.g., at least one. For instance, the disclosure of "a stream," "a disproportionation catalyst," "an inert solvent", and the like, is meant to encompass one, or mixtures or combinations of more than one stream, disproportionation catalyst, inert solvent, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, that a stream including ethylene and a dimerization catalyst may be contacted at a pressure of about 1034 kPa to about 1724 kPa. This range should be interpreted as encompassing pressures of about 1034 kPa to about 1724 kPa, and further encompasses "about" each of 1041 kPa, 1048 kPa, 1054 kPa, 1061 kPa, 1069 kPa, 1076 kPa, 1082 kPa, 1089 kPa, 1096 kPa, 1103 kPa, 1110 kPa, 1117 kPa, 1124 kPa, 1131 kPa, 1138 kPa, 1145 kPa, 1151 kPa, 1158 kPa, 1165 kPa, 1172 kPa, 1179 kPa, 1186 kPa, 1193 kPa, 1200 kPa, 1207 kPa, 1213 kPa, 1220 kPa, 1227 kPa, 1234 kPa, 1241 kPa, 1248 kPa, 1255 kPa, 1262 kPa, 1269 kPa, 1276 kPa, 1282 kPa, 1289 kPa, 1296 kPa, 1303 kPa, 1310 kPa, 1317 kPa, 1324 kPa, 1331 kPa, 1338 kPa, 1344 kPa, 1351 kPa, 1358 kPa, 1365 kPa, 1372 kPa, 1379 kPa, 1386 kPa, 1393 kPa, 1400 kPa, 1407 kPa, 1413 kPa, 1420 kPa, 1427 kPa, 1434 kPa, 1441 kPa, 1448 kPa, 1455 kPa, 1462 kPa, 1469 kPa, 1475 kPa, 1482 kPa, 1489 kPa, 1496 kPa, 1503 kPa, 1510 kPa, 1517 kPa, 1524 kPa, 1531 kPa, 1538 kPa, 1544 kPa, 1551 kPa, 1558 kPa, 1565 kPa, 1572 kPa, 1579 kPa, 1586 kPa, 1593 kPa, 1600 kPa, 1606 kPa, 1613 kPa, 1620 kPa, 1627 kPa, 1634 kPa, 1641 kPa, 1648 kPa, 1655 kPa, 1662 kPa, 1669 kPa, 1675 kPa, 1682 kPa, 1689 kPa, 1696 kPa, 1703 kPa, 1710 kPa, and 1717 kPa, including any ranges and sub-ranges between any of these values.

EXAMPLES

The present disclosure is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present disclosure or the scope of the appended claims. Thus, other aspects of this disclosure will be apparent to those skilled in the art from consideration of the specification and practice of the disclosure disclosed herein.

Example 1—Ethylene Dimerization

A 300 mL Parr reactor was used for the ethylene dimerization of this example. A bake-out of the reactor was conducted with a dry inert gas purge at 120° C. for 1 hour, followed by a cool-down to the desired process temperature, which for this example was about 50° C. Argon was used for the dry inert gas purge of this example, but other gases, such as nitrogen, may be used.

The reactor was then primed with ethylene. A solvent, cocatalyst, and catalyst were subsequently added before the reactor was pressurized to 1310 kPa for the ethylene dimerization. The solvent of this example was heptane, but other inert solvents, such as hexane or chlorobenzene, may be used.

Under a constant reactor pressure, the consumption of ethylene was monitored by a mass flow meter. A run was terminated when the mass flow meter indicated that no more ethylene consumption was occurring or a 30 minute runtime was reached, whichever came first. The reactor overhead and liquid products were analyzed separately via vapor and liquid gas chromatographs (GCs).

Table 1 depicts the results of the ethylene dimerization of this example using 67.9 wtppm of $(n\text{-}Bu_3P)_2NiCl_2$ in 100 mL heptane solvent and an ethylaluminum dichloride (EADC) to Ni molar ratio of 3 at 1344 kPa and 51.3° C. for 30 minutes.

TABLE 1

Ethylene Dimerization with $(n\text{-}Bu_3P)_2NiCl_2$ catalyst and EADC cocatalyst.

| Catalyst | | Reactor Conditions | | | |
|---|---|---|---|---|---|
| | Ni usage (wtppm) | Al/Ni molar | Rxn P (kPa) | Rxn T (° C.) | Rxnt (min) |
| $(nBu_3P)_2NiCl_2$ | 67.9 | 3 | 1344 | 51.3 | 30 |
| | | Product Analysis | | | |
| | C2 = (adj wt %) | B1 sel (wt %) | CB2 set (wt %) | TB2 sel (wt %) | C4 sel (wt %) |
| | 8.3 | 15.7 | 34.1 | 48.6 | 98.4 |
| | C6 sel (wt %) | Productivity (g/g) | B2/B (%) | Prod (g/mol) | |
| | 1.6 | 18036 | 84 | 9.64E+06 | |

As depicted at Table 1, the ethylene dimerization of this example achieved 91.7% ethylene conversion (8.3 wt % ethylene remaining in the product), and 98.4 wt % selectivity toward butenes, with 84% in the form of 2-butenes (both cis and trans).

We claim:

1. A method of making propylene and alkylate, the method comprising:
   providing a stream comprising n-butenes, wherein the providing of the stream comprising n-butenes comprises contacting a first stream comprising ethylene with a dimerization catalyst to form the stream comprising n-butenes, wherein the stream comprising n-butenes further comprises unconsumed ethylene;
   contacting the stream comprising n-butenes with a second stream comprising ethylene in the presence of a disproportionation catalyst to form a stream comprising propylene and $C_{4+}$ olefins;
   removing propylene from the stream comprising propylene and $C_{4+}$ olefins to form a stream comprising $C_{4+}$ olefins; and
   contacting the stream comprising $C_{4+}$ olefins with a stream comprising isobutane in the presence of an alkylation catalyst to form alkylate.

2. The method of claim 1, wherein the stream comprising n-butenes comprises 2-butenes.

3. The method of claim 2, wherein the weight percentage of the 2-butenes in the stream comprising n-butenes is about 50% to 100%, based on the weight of the stream comprising n-butenes.

4. The method of claim 1, wherein the dimerization catalyst comprises a transition metal catalyst.

5. The method of claim 4, wherein the transition metal catalyst comprises Ti, Cr, Ni, Fe, Zr, or a combination thereof.

6. The method of claim 4, wherein the dimerization catalyst further comprises a cocatalyst.

7. The method of claim 6, wherein the cocatalyst comprises an aluminum alkyl, an organoborane, or a combination thereof.

8. The method of claim 7, wherein the aluminum alkyl comprises triethylaluminum (TEA), ethylaluminum dichloride (EADC), or a combination thereof.

9. The method of claim 7, wherein the organoborane comprises tris(pentafluorophenyl) borane.

10. The method of claim 1, wherein the stream comprising n-butenes further comprises $C_{6+}$ olefins.

11. The method of claim 10, further comprising removing the $C_{6+}$ olefins from the stream comprising n-butenes prior to the contacting of the stream comprising n-butenes with the second stream comprising ethylene.

12. The method of claim 1, wherein the stream comprising propylene and $C_{4+}$ olefins further comprises ethylene.

13. The method of claim 12, further comprising removing the ethylene from the stream comprising propylene and $C_{4+}$ olefins to form a third stream comprising ethylene prior to removing propylene from the stream comprising propylene and $C_{4+}$ olefins.

14. The method of claim 12, further comprising removing the ethylene from the stream comprising propylene and $C_{4+}$ olefins to form a third stream comprising ethylene prior to contacting the stream comprising $C_{4+}$ olefins with the stream comprising isobutane.

15. The method of claim 1, wherein the disproportionation catalyst comprises a transition metal oxide.

16. The method of claim 15, wherein the transition metal oxide comprises a transition metal selected from Group VIB to Group VIIIB of the periodic table.

17. The method of claim 15, wherein the transition metal oxide comprises W, Mo, Re, Ru, or a combination thereof.

18. The method of claim 1, wherein the stream comprising propylene and $C_{4+}$ olefins further comprises 1-butene and 2-butene, and the amount of 1-butene in the stream comprising propylene and $C_{4+}$ olefins is greater than the amount of 1-butene in the stream comprising n-butenes.

19. The method of claim 1, wherein the stream comprising propylene and $C_{4+}$ olefins further comprises 1-butene and 2-butene, and the amount of 1-butene in the stream comprising propylene and $C_{4+}$ olefins is greater than the amount of 2-butene in the stream comprising propylene and $C_{4+}$ olefins.

20. A method of making propylene and alkylate, the method comprising:
   contacting a first stream comprising ethylene with a dimerization catalyst to form a stream comprising n-butenes and $C_{6+}$ olefins;
   removing the $C_{6+}$ olefins from the stream comprising n-butenes and $C_{6+}$ olefins to form a stream comprising n-butenes;

contacting the stream comprising n-butenes with a second stream comprising ethylene in the presence of a disproportionation catalyst to form a stream comprising ethylene, propylene, and $C_{4+}$ olefins;

removing ethylene from the stream comprising ethylene, propylene, and $C_{4+}$ olefins to form a stream comprising propylene and $C_{4+}$ olefins and a third stream comprising ethylene, wherein the third stream comprising ethylene is (i) combined with the second stream comprising ethylene, (ii) combined with the stream comprising n-butenes, or (iii) disposed in a disproportionation unit that contains the disproportionation catalyst;

removing propylene from the stream comprising propylene and $C_{4+}$ olefins to form a stream comprising $C_{4+}$ olefins; and contacting the stream comprising $C_{4+}$ olefins with a stream comprising isobutane in the presence of an alkylation catalyst to form alkylate.

* * * * *